United States Patent [19]
Montagna et al.

[11] 4,371,428
[45] * Feb. 1, 1983

[54] SEPARATING VINYLTOLUENE FROM OTHER ALKENYLAROMATICS

[75] Inventors: John C. Montagna, O'Hara Township, Allegheny County; Robert D. Galli, New Kensington, both of Pa.; John Freel, Parker, Colo.

[73] Assignee: Gulf Research & Development Company, Pittsburgh, Pa.

[*] Notice: The portion of the term of this patent subsequent to Jul. 28, 1998, has been disclaimed.

[21] Appl. No.: 209,596

[22] Filed: Nov. 24, 1980

[51] Int. Cl.$^3$ .............................................. B01D 3/40
[52] U.S. Cl. ........................................ 203/51; 203/58; 208/347; 585/808

[58] Field of Search ............... 585/808, 807, 857, 864, 585/865, 833, 856, 857, 860; 208/347; 203/58, 57, 51, 60, 71, 59, 61-65

[56] References Cited

U.S. PATENT DOCUMENTS

| | | | |
|---|---|---|---|
| 3,210,259 | 10/1965 | Cornell et al. | 203/58 |
| 3,953,300 | 4/1976 | Ginnasi et al. | 585/808 |
| 4,280,881 | 7/1981 | Montagana et al. | 203/51 |

Primary Examiner—Frank Sever
Attorney, Agent, or Firm—Deane E. Keith; Forrest D. Stine; Donald L. Rose

[57] ABSTRACT

Vinyltoluene is separated from close-boiling, olefinically unsaturated alkylaromatic compounds by extractive distillation. For example, vinyltoluene is separated from cis-β-methylstyrene, and from α-methylstyrene by extractive distillation using γ-butyrolactone as the extracting agent.

13 Claims, No Drawings

SEPARATING VINYLTOLUENE FROM OTHER ALKENYLAROMATICS

SUMMARY OF THE INVENTION

This invention relates to a process of separating vinyltoluene from close-boiling aromatic compounds by extractive distillation, and more particularly it relates to the separation of vinyltoluene from close-boiling mono-olefinically unsaturated alkylaromatic compounds by extractive distillation.

DESCRIPTION OF THE INVENTION

Mixtures of close-boiling aromatic compounds are produced in large quantities in various industrial and petroleum refinery operations. Where the scale of manufacture is very large, the total amount of the individual components in the mixture can be large even though the relative amount of a specific component is small. This is particularly true in the industrial pyrolysis of petroleum fractions, such as the naphthas and gas oils, for the production of ethylene and other low boiling components.

The pyrolysis of these higher boiling petroleum fractions results in a complex by-product liquid mixture of many dozens of compounds including a six to ten carbon, predominately aromatic component. Rather than using this entire liquid by-product as a fuel, it would be desirable individually to separate out those constituents which have a substantial commercial utility. However, due to the occurrence of many isomers and analogs having boiling points close to the desired compounds, clear separation of many of the individual compounds by distillation has heretofore been difficult or impossible.

The separation of olefinically unsaturated alkylaromatic compounds from close-boiling saturated alkylaromatics, such as o-vinyltoluene from o-ethyltoluene and indene from indane, by extractive distillation using pyrrolidones is described in U.S. Pat. No. 3,210,259. However, the separation of mono-olefinically unsaturated alkylaromatic compounds from other close-boiling mono-olefinically unsaturated alkylaromatic compounds is not disclosed.

We have now surprisingly discovered that certain polar compounds can be used to assist in the separation of vinyltoluene from mixtures containing different close-boiling aromatic mono-olefins, such as α-methylstyrene and cis-β-methylstyrene by extractive distillation. Thus, we have surprisingly discovered that when the polar compound is present, it preferentially associates itself with one group of olefinic compound, the vinyltoluenes, in some manner to hold them back and permit the other olefinic compounds, such as cis-β-methylstyrene and α-methylstyrene, to be recovered in the vapor phase. In short, the polar solvent, surprisingly increases the relative volatility of various aromatic mono-olefins, including α-methylstyrene and cis-β-methylstyrene, with respect to vinyltoluene, a different close-boiling aromatic mono-olefin.

The three close-boiling isomeric vinyltoluenes, namely, o-, m- and p-vinyltoluene are not separated one from the others by our process. Instead if any two or all three of these vinyltoluenes are associated together in the mixture undergoing separation, these vinyltoluenes will be separated as a group from the saturated alkylaromatics and the other mono-olefinically unsaturated alkylaromatic compounds. Therefore, when the expression vinyltoluene is used herein, it is intended to mean any single isomer or combination of two isomers or all three vinyltoluene isomers, as the case may be.

The polar compounds which we find useful as an agent in the extractive distillation are oxygen-containing, nitrogen-containing and sulfur-containing polar compounds having boiling points within a desired range. This class of polar compounds includes sulfolane, 2-pyrrolidone, the N-lower alkyl-2-pyrrolidones such as N-methyl-2-pyrrolidone, γ-butyrolactone, ethylene carbonate, tetramethylene sulfoxide, the di- lower alkyl sulfoxides such as dimethyl sulfoxide, ε-caprolactam, and the like.

The solvent not only enhances the relative volatility of the olefinic components undergoing separation from the vinyltoluene, but also it desirably possesses a boiling point within an optimum range. That is, the boiling point of the extractive solvent should be between about 185° and about 300° C., and preferably between about 190° and about 250° C. If the boiling point of the solvent should be below that of vinyltoluene, the solvent would leave the distillation column with the vapor and as a result fail to perform its function of holding back the vinyltoluene. If the solvent's boiling point is too close to that of vinyltoluene, it will perform its function but will itself be difficult to separate from vinyltoluene. And as the boiling point of the solvent becomes high, it tends to separate in the extraction column downwardly from the vinyltoluene thereby also losing its effectiveness. Additionally, solvents with boiling points excessively higher than vinyltoluene have the tendency of imposing higher heat loads on the distillation because of the higher heats of vaporization and higher heat capacities, which characteristics are typical of the higher boiling solvents.

This process can be used to separate vinyltoluene from a mixture containing other mono-olefinically unsaturated alkylaromatic compounds having boiling points close to vinyltoluene regardless of the source of the mixture. A particularly rich potential source of vinyltoluene is the pyrolysis gasoline stream resulting from the pyrolysis of heavier hydrocarbons including naphtha, gas oil and the like obtained as a by-product in the production of gaseous olefins. This pyrolysis gasoline, which is a mixture of paraffinic, aromatic and mixed paraffinic-aromatic hydrocarbons having between about five and about ten carbon atoms, generally contains several percent vinyltoluene.

In order to more effectively use the extractive distillation procedure of the instant invention to recover the vinyltoluene from pyrolysis gasoline or any similar mixture, it is desirable to concentrate the vinyltoluene by ordinary fractional distillation into a vinyltoluene-rich concentrate. This can be accomplished in two stages in which a light fraction boiling lower than vinyltoluene is taken off in the first stage. The bottoms containing the vinyltoluene is then fractionated in the second stage at more rigorous conditions to obtain the vinyltoluene-rich concentrate as the overhead fraction, which is thereby separated from the higher boiling elements remaining in the tower bottoms. This overhead vinyltoluene-rich fraction also containing a substantial quantity of both alkenyl- and alkylaromatic compounds having boiling points close to vinyltoluene, is then ready for the extractive distillation. The relative amount of vinyltoluene in this fraction will depend on a number of factors including the amount of vinyltoluene in the pyrolysis gasoline itself and the efficiency of each of the preceding concentrating distillation stages.

The extractive distillation can be used to recover vinyltoluene from a mixture containing any amount of vinyltoluene but it is preferred that the vinyltoluene in the close-boiling mixture undergoing extraction comprise at least about ten percent of the total quantity of the close-boiling mixture and it is most preferred that the vinyltoluene comprise at least about 25 percent in order to significantly improve the overall economics of the recovery procedure. Additionally, although any amount of the extractive solvent will benefit the separation, we prefer that the weight ratio of the extractive solvent to the close-boiling hydrocarbon mixture undergoing extraction be at least about 0.2:1 and most preferably at least about 1:1 up to a maximum preferred weight ratio of about 5:1 and most preferably a maximum of about 3:1.

The extractive distillation can be carried out at atmospheric pressure but it is preferred that this distillation be carried out at reduced pressure in order to reduce the operating temperature and thereby minimize the polymerization of the olefinic constituents present in the column. Therefore, an operating pressure from about 25 mm Hg up to 760 mm and higher can be used, but it is preferred that the operating pressure as measured at the top of the distillation column be between about 30 and about 100 mm Hg. Additionally, a suitable polymerization inhibitor can be used in the extractive distillation column.

DESCRIPTION OF PREFERRED EMBODIMENTS

EXAMPLE 1

The vinyltoluene was recovered from the eight carbon and higher fraction, Stream A, resulting from the commercial pyrolysis of gas oil and naphtha in the production of ethylene and propylene. The vinyltoluene concentration in Stream A of 16.44 weight percent was increased to 43.91 percent in Stream B in preparation for extractive distillation by two stages of distillation which removed, first the more volatile components and second the less volatile components. Stream B was mixed with γ-butyrolactone in a 1:1 weight ratio for the extractive distillation. The extractive distillation was carried out in a column having an internal diameter of one inch (2.54 cm) and packed with 66 inches (168 cm) of metal springs. The column was operated at a reflux ratio of 5:1 and a temperature of 87° C. and a pressure of 65 mm of mercury, absolute, at the reflux condenser. The concentration of vinyltoluene was increased to 96.46 percent in the tower bottoms stream, Stream C, excluding the γ-butyrolactone solvent. The complete analyses of Streams A, B and C exclusive of the γ-butyrolactone extractive solvent is set out in Table I.

TABLE 1

| Component | Stream, wt. % | | | b.p., °C. |
|---|---|---|---|---|
| | A | B | C | |
| light components | 45.17 | — | — | — |
| 1,3,5-trimethylbenzene | 2.68 | 7.84 | 0.04 | 164.7 |
| 1-ethyl-2-methylbenzene | 0.65 | 1.86 | — | 165.2 |
| α-methylstyrene | 0.92 | 3.01 | 0.19 | 165.5 |
| cis-β-methylstyrene | 0.56 | 1.90 | 0.19 | 167.5 |
| 1,2,4-trimethylbenzene | 5.07 | 30.95 | 0.31 | 169.4 |
| vinyltoluene | 16.44 | 43.91 | 96.46 | 170–173 |
| unknown | 0.82 | 1.02 | 0.81 | — |
| 1,2,3-trimethylbenzene | 1.28 | 0.60 | 0.98 | 176 |
| indane | 2.91 | 0.47 | 0.87 | 178 |

TABLE 1-continued

| Component | Stream, wt. % | | | b.p., °C. |
|---|---|---|---|---|
| | A | B | C | |
| trans-β-methylstyrene | | | | 178 |
| indene | 12.11 | 0.07 | — | 182.6 |
| heavy components | 14.30 | — | — | — |

Following the extractive distillation, the solvent and vinyltoluene product are separated by distillation. This separation can further purify the vinyltoluene product of the higher boiling impurities. Since the solvent was not removed in the above experiment, this final purification is demonstrated in the following example in which the extractive distillation tower bottoms feed was from a different source.

EXAMPLE 2

Sufficient bottoms product, Stream C', from an extractive distillation procedure operated as described in Example 1 was collected to subject it to distillation for recovery of the vinyltoluene component. The γ-butyrolactone solvent comprised about 75 percent of this bottoms solution. The distillation column was operated at a reflux ratio of 10:1, a temperature of 83° C. and a pressure at the top of 60 mm of mercury. The vinyltoluene, Stream D', was recovered overhead. The analyses of these two streams, excluding the solvent is set out in Table II.

TABLE II

| Component | Stream C' | Stream D' |
|---|---|---|
| 1,3,5-trimethylbenzene | 0.02 | 0.04 |
| α-methylstyrene | 0.21 | 0.32 |
| cis-β-methylstyrene | 0.21 | 0.32 |
| 1,2,4-trimethylbenzene | 0.41 | 0.10 |
| vinyltoluene | 95.5 | 97.88 |
| unknowns | 1.15 | 0.48 |
| 1,2,3-trimethylbenzene | 1.14 | 0.57 |
| trans-β-methylstyrene indane | 1.06 | 0.29 |

EXAMPLE 3

A number of organic polar compounds were tested to evaluate whether the compounds would increase the relative volatility between several close-boiling hydrocarbons and vinyltoluene when compared with the relative volatility in the absence of the polar solvent. The close-boiling hydrocarbons that were used were 1,2,4-trimethylbenzene(1,2,4-TMB); α-methylstyrene(α-MS) and cis-β-methylstyrene(cis-β-MS). The relative volatilities as determined from these experiments are set out in Table III. All data were obtained at a temperature of 90° C. by operating the single stage distillation at reduced pressure. The solvent to total hydrocarbon weight ratio (S/t.HC) as listed in the table is based on the total quantity of solvent-free hydrocarbons initially present in the solution. The vinyltoluene portion (VT) was a 50:50 weight mixture of 3- and 4-vinyltoluene and this vinyltoluene portion comprised 50 weight percent of the total hydrocarbons in the mixture.

TABLE III

| Solvent | S t.HC | 1,2,4-TMB VT | α-MS VT | cis-β-MS VT |
|---|---|---|---|---|
| none | 0 | 1.08 | 1.15 | 1.10 |

TABLE III-continued

| Solvent | S t.HC | 1,2,4-TMB VT | α-MS VT | cis-β-MS VT |
|---|---|---|---|---|
| 2-pyrrolidone | 1 | 1.41 | 1.18 | 1.16 |
| | 2 | 1.48 | 1.20 | 1.17 |
| N—methylpyrrolidone | 1 | 1.33 | 1.24 | 1.14 |
| | 2 | 1.41 | 1.27 | 1.15 |
| dimethylsulfoxide | 1 | 1.38 | 1.19 | 1.14 |
| | 2 | 1.46 | 1.19 | 1.16 |
| ethylene carbonate | 1 | 1.47 | 1.20 | 1.17 |
| | 2 | 1.49 | 1.20 | 1.27 |
| γ-butyrolactone | 1 | 1.33 | 1.23 | 1.19 |
| | 2 | 1.47 | 1.22 | 1.18 |

If the concentration of vinyltoluene in the bottoms product from the extractive distillation procedure does not reach the predetermined goal, this vinyltoluene-enriched product can be subjected to one or more additional extractive distillations until the desired concentration of vinyltoluene of the enriched product is reached or exceeded.

It is to be understood that the above disclosure is by way of specific example and that numerous modifications and variations are available to those of ordinary skill in the art without departing from the true spirit and scope of the invention.

We claim:

1. The method of separating vinyltoluene in admixture with at least one close-boiling mono-olefinically unsaturated alkylaromatic compound by extractive distillation which comprises distilling said mixture comprising vinyltoluene and at least one close-boiling mono-olefinically unsaturated alkylaromatic compound in the presence of at least one liquid oxygen-containing, sulfur-containing or nitrogen-containing organic polar compound having a boiling point at 760 mm Hg of between about 185° and about 300° C., recovering a vapor phase rich in said close-boiling mono-olefinically unsaturated alkylaromatic compound and recovering a bottoms fraction comprising vinyltoluene and said organic polar compound.

2. The method of separating vinyltoluene in admixture with at least one-close boiling mono-olefinically unsaturated alkylaromatic compound by extractive distillation in accordance with claim 1 in which the olefinically unsaturated alkylaromatic compound includes at least one component selected from α-methylstyrene, cis-β-methylstyrene, and mixtures thereof.

3. The method of separating vinyltoluene in admixture with at least one close-boiling mono-olefinically unsaturated alkylaromatic compound by extractive distillation in accordance with claim 2 wherein the polar compound is sulfolane, 2-pyrrolidone, γ-butyrolactone, ethylene carbonate, tetramethylene sulfoxide, ε-caprolactam, an N-lower alkyl-2-pyrrolidone, a di-lower alkyl sulfoxide, or a mixture thereof.

4. The method of separating vinyltoluene in admixture with at least one close-boiling mono-olefinically unsaturated alkylaromatic compound by extractive distillation in accordance with claim 3 in which the polar solvent is N-methyl-2-pyrrolidone.

5. The method of separating vinyltoluene in admixture with at least one close-boiling mono-olefinically unsaturated alkylaromatic compound by extractive distillation in accordance with claim 3 in which the polar solvent is γ-butyrolactone.

6. The method of separating vinyltoluene in admixture with at least one close-boiling mono-olefinically unsaturated alkylaromatic compound by extractive distillation in accordance with claim 3 in which the vinyltoluene is recovered from said bottoms fraction by distillation.

7. The method of separating vinyltoluene in admixture with at least one close-boiling mono-olefinically unsaturated alkylaromatic compound by extractive distillation in accordance with claim 3 in which the polar solvent is ethylene carbonate.

8. The method of separating vinyltoluene in admixture with at least one close-boiling mono-olefinically unsaturated alkylaromatic compound by extractive distillation in accordance with claim 3 in which the polar solvent is 2-pyrrolidone.

9. The method of separating vinyltoluene in admixture with at least one close-boiling mono-olefinically unsaturated alkylaromatic compound by extractive distillation in accordance with claim 1 in which the vinyltoluene comprises at least about ten percent of said mixture.

10. The method of separating vinyltoluene in admixture with at least one close-boiling mono-olefinically unsaturated alkylaromatic compound by extractive distillation in accordance with claim 1 in which the weight ratio of said organic polar compound to the hydrocarbon components in said mixture is between about 0.2:1 and about 5:1.

11. The method of separating vinyltoluene in admixture with at least one close-boiling mono-olefinically unsaturated alkylaromatic compound by extractive distillation in accordance with claim 1 in which the boiling point of the organic polar compound is between about 190° and about 250° C.

12. The method of separating vinyltoluene in admixture with at least one close-boiling mono-olefinically unsaturated alkylaromatic compound by extractive distillation in accordance with claim 1 in which the vinyltoluene comprises at least about 25 percent of said mixture.

13. The method of separating vinyltoluene in admixture with at least one close-boiling mono-olefinically unsaturated alkylaromatic compound by extractive distillation in accordance with claim 1 in which the weight ratio of said organic polar compound to the hydrocarbon portion of said mixture is between about 1:1 and about 3:1.

* * * * *

UNITED STATES PATENT OFFICE
CERTIFICATE OF CORRECTION

Patent No. 4,371,428  Dated February 1, 1983

Inventor(s) John C. Montagna, Robert D. Galli and John Freel

It is certified that error appears in the above-identified patent and that said Letters Patent are hereby corrected as shown below:

Col. 3, lines 68-69, and Col. 4, lines 5-7,
the last four lines of Table 1 should read as follows:

| | | | | |
|---|---|---|---|---|
| 1,2,3-trimethylbenzene | 1.28 | 0.60 | 0.98 | 176 |
| indane<br>trans-β-methylstyrene | 2.91 | 0.47 | 0.87 | 178<br>178 |
| indene | 12.11 | 0.07 | -- | 182.6 |
| heavy components | 14.30 | -- | -- | -- |

Signed and Sealed this

Twenty-eighth Day of June 1983

[SEAL]

Attest:

GERALD J. MOSSINGHOFF

Attesting Officer   Commissioner of Patents and Trademarks